United States Patent
Costantini

(10) Patent No.: US 11,191,820 B2
(45) Date of Patent: Dec. 7, 2021

(54) METHOD FOR INDUCING EARLY T MEMORY RESPONSE WITH SHORT PEPTIDES ANTI-TUMOR VACCINE

(71) Applicant: OSE IMMUNOTHERAPEUTICS, Nantes (FR)

(72) Inventor: Dominique Costantini, Paris (FR)

(73) Assignee: OSE Immunotherapeutics, Nantes (FR)

( * ) Notice: Subject to any disclaimer, the term of this patent is extended or adjusted under 35 U.S.C. 154(b) by 308 days.

(21) Appl. No.: 15/578,721

(22) PCT Filed: Jun. 29, 2015

(86) PCT No.: PCT/EP2015/064746
§ 371 (c)(1),
(2) Date: Dec. 1, 2017

(87) PCT Pub. No.: WO2017/000983
PCT Pub. Date: Jan. 5, 2017

(65) Prior Publication Data
US 2018/0169200 A1    Jun. 21, 2018

(51) Int. Cl.
*A61K 39/00* (2006.01)
*A61P 35/04* (2006.01)
*A61K 39/39* (2006.01)

(52) U.S. Cl.
CPC .......... *A61K 39/0011* (2013.01); *A61K 39/39* (2013.01); *A61P 35/04* (2018.01); *A61K 2039/5158* (2013.01); *A61K 2039/545* (2013.01); *A61K 2039/55* (2013.01); *A61K 2039/555* (2013.01); *A61K 2039/70* (2013.01)

(58) Field of Classification Search
CPC ................................................ A61K 39/0011
See application file for complete search history.

(56) References Cited

U.S. PATENT DOCUMENTS

| | | | | |
|---|---|---|---|---|
| 8,007,810 B2* | 8/2011 | Fikes | .................. | A61K 39/0011 424/185.1 |
| 9,394,350 B2* | 7/2016 | Fikes | .................. | A61K 39/0011 |
| 9,913,884 B2* | 3/2018 | Fikes | ...................... | A61P 35/04 |
| 10,434,157 B2* | 10/2019 | Costantini | ............... | A61P 35/00 |
| 2008/0274129 A1* | 11/2008 | Fikes | .................. | A61K 39/0011 424/185.1 |
| 2010/0209493 A1* | 8/2010 | Fikes | ....................... | C07K 7/06 424/450 |
| 2012/0183598 A1* | 7/2012 | Fikes | ..................... | A61K 39/39 424/450 |
| 2014/0141064 A1* | 5/2014 | Fikes | ..................... | C07K 14/47 424/450 |
| 2017/0028041 A1* | 2/2017 | Fikes | ..................... | C07K 14/47 |

FOREIGN PATENT DOCUMENTS

JP    2006-526628   11/2006
WO   WO 2004/094454  11/2004

OTHER PUBLICATIONS

Beebe et al. (Hum. Vaccin. May-Jun. 2008; 4 (3): 210-8).*
Stancovski et al. (Proc. Natl. Acad. Sci. USA. Oct. 1, 1991; 88 (19): 8691-5).*
Chin et al. (Chang Gung Med J. Jan.-Feb. 2008; 31 (1): 1-15).*
Jiang et al. (J. Biol. Chem. Feb. 11, 2005; 280 (6): 4656-4662).*
Riemer et al. (Mol. Immunol. 2005; 42: 1121-1124).*
Ingram et al. (Proc. Natl. Acad. Sci. USA. Apr. 10, 2018; 115 (15): 3912-3917).*
Oh et al. (Mol. Cells. Dec. 2012; 34 (6): 523-9).*
Brodská et al. (Cancer Immunol. Res. Oct. 2016; 4 (10): 815-819).*
Barve et al. (J. Clin. Oncol. Sep. 20, 2008; 26 (27): 4418-25).*
Garon et al. (N. Engl. J. Med. May 21, 2015; 372 (21): 2018-28).*
Woodland (Trends Immunol. Feb. 2004; 25 (2): 98-104).*
Marshall et al. (J. Clin. Oncol. Dec. 1, 2000; 18 (23): 3964-73).*
Barve, M. et al. "Induction of Immune Responses and Clinical Efficacy in a Phase II Trial of IDM-2101, a 10-Epitope Cytotoxic T-Lymphocyte Vaccine, in Metastatic Non-Small-Cell Lung Cancer" *Journal of Clinical Oncology*, Sep. 20, 2008, pp. 4418-4425, vol. 26, No. 27.
ClinicalTrials.gov [online], "Vaccine Therapy in Treating Patients With Stage IIIB, Stage IV, or Recurrent Non-Small Cell Lung Cancer" Nov. 5, 2013, retrieved on Mar. 14, 2016, retrieved from the internet, URL: https://clinicaltrials.qov/ct2/show/NCT00104780?term=NCT00104780&rank=1, pp. 1-4.
Written Opinion in International Application No. PCT/EP2015/064746, dated Mar. 31, 2016, pp. 1-6.
Brahmer, J.R. et al. "Immune Checkpoint Inhibitors: Making Immunotherapy a Reality for the Treatment of Lung Cancer" *Cancer Immunolology Research*, Aug. 2013, pp. 85-91, vol. 1, No. 2.
Holmes, J.P. et al. "Optimal Dose and Schedule of an HER-2/neu (E75) Peptide Vaccine to Prevent Breast Cancer Recurrence" *Cancer*, 2008, pp. 1666-1675, vol. 113, No. 7.

(Continued)

*Primary Examiner* — Stephen L Rawlings
(74) *Attorney, Agent, or Firm* — Saliwanchik, Lloyd & Eisenschenk

(57) ABSTRACT

The present invention relates to a therapeutic peptide T specific immune therapy for use in the treatment of a cancer of an HLA-A2 (Human Leukocyte Antigen A2) positive patient, said treatment comprises a priming period consisting in two to three administrations of said therapeutic peptide T specific immune therapy, thereby inducing a memory T cell response.

15 Claims, 2 Drawing Sheets
Specification includes a Sequence Listing.

(56) References Cited

OTHER PUBLICATIONS

Walter, S. et al. "Multipeptide immune response to cancer vaccine IMA901 after single-dose cyclophosphamide associates with longer patient survival" *Nature Medicine*, Aug. 2012, pp. 1254-1261, Online Methods pp. 1-4, vol. 18, No. 8.
Alexander, J. et al. "Development of High Potency Universal DR-Restricted Helper Epitopes by Modification of High Affinity DR-Blocking Peptides" *Immunity*, Dec. 1994, pp. 751-761, vol. 1.

* cited by examiner

ID No 10, with X and a respectively indicating cyclohexy-

METHOD FOR INDUCING EARLY T MEMORY RESPONSE WITH SHORT PEPTIDES ANTI-TUMOR VACCINE

CROSS-REFERENCE TO RELATED APPLICATION

This application is the U.S. national stage application of International Patent Application No. PCT/EP2015/064746, filed Jun. 29, 2015.

FIELD OF THE INVENTION

The present invention relates to the field of medicine, in particular of oncology, and more particularly the present invention relates to the treatment of cancer.

The Sequence Listing for this application is labeled "Seq-List-replace.txt" which was created on Oct. 28, 2020 and is 3 KB. The entire content of the sequence listing is incorporated herein by reference in its entirety.

BACKGROUND OF THE INVENTION

Memory T cells are a subset of antigen-specific T cells that persist long-term after having encountered and responded to their cognate antigen. They quickly expand to large numbers of effector T cells upon re-exposure to their cognate antigen, thus providing the immune system with "memory" against past infections as well as cancer cells. At the second encounter with the invader or cancer cells, memory T cells can initiate a faster and stronger immune response than the first time. Memory T cells comprise two subtypes: central memory T cells (TCM cells) and effector memory T cells (TEM cells). Memory cells may be either $CD4^+$ or $CD8^+$.

It has recently been established, for several human cancers, that high densities of effector memory $CD8^+$ cytotoxic T cells are associated with a longer overall survival (Fridman W. et al, 2012, *Nat Rev Cancer*, 12(4), 298-306). Central memory T cells appears however to have an even greater capacity to persist in vivo and are also more efficient in mediating protective immunity because of their increased proliferative capacity (Calarota S A et al, 2013, *Clinical and Developmental Immunology*, Article ID 637649).

In the literature, data indicate that an initial proper activation of the $CD8^+$ T cell response by peptide vaccines in mineral oil adjuvant does not ensure long-term effectiveness of these $CD8^+$ T cells (Bijker M S et al, 2007, *J Immunol*, 179:5033-5040), although, such a long-term effectiveness would be of huge interest in the field of chronic diseases such as cancer.

Bijker et al described a specific strategy linked to the use of long peptides to overcome the poor long term effectiveness of cancer vaccines. However, this strategy was shown unreliable by Karkada et al. (Karkada M et al, 2014, *Biologics: Target and Therapy*, 8: 27-38). Indeed, the immune response with such long peptides was not constant at each time point and was decreasing after the first injection.

Thus, there is still a strong need, nowadays, to develop a method of treatment with peptide cancer vaccine that would be able to stimulate memory T cells as early as possible, especially central memory T cells.

The classical administration regimen of short peptide cancer vaccines rely on at least 5-6 administrations of the vaccine. Holmes et al. (defines the optimal scheme of administration of a specific short peptide cancer vaccine as 6 injections of vaccine for each month of treatment (Holmes J P et al, 2008, *Cancer*, 113, 1666-1675). In a phase two trial, subjects were considering to be effectively part of the vaccination protocol if they had received at least 6 administrations of the vaccine (Walter S et al, 2012, *Nature Medicine*, 18, 1254-126). Seven to ten short peptide vaccine administration were considered by others for an effective treatment (Kantoff P W et al, 2010, *Cancer J Clin Oncol*, 28:1099-1105; Schwartzentruber D J et al, 2011, *N Engl J Med*, 364:2119-27).

These short peptide vaccine treatments can be painful for the subjects and are not devoid of side effects and toxicity. In addition, controlling health care costs and optimizing cancer treatment are key issues in consideration of the rise of costs. There is thus a strong need to find new methods allowing to modify the scheme of administration of the vaccine so as to reduce the number of injections while obtaining a memory T response as early as possible.

SUMMARY OF THE INVENTION

The object of the present invention relates to a new administration regimen of a short peptide cancer vaccine allowing an early memory T cells response. In this invention, the inventors surprisingly showed that no more than three administrations of the short peptide combination were sufficient to obtain a T specific Immune response through memory T Cells and this immune response was linked with a longer time to progression (TTP).

The present invention relates to a therapeutic peptide T specific immune therapy for use in the treatment of a cancer of an HLA-A2 (Human Leukocyte Antigen A2) positive patient, wherein the therapeutic peptide T specific immune therapy comprises the peptide aKXVAAWTLKAAa (SEQ ID No 10, with X and a respectively indicating cyclohexylalanine and d-alanine) and at least 4, 5, 6, 7, 8 or 9 peptides selected from the group consisting of RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), and YLSGADLNL (SEQ ID No 9), and wherein said treatment comprises a priming period consisting in two to three administrations of said therapeutic peptide T specific immune therapy, thereby inducing a central memory T cell response.

In a preferred embodiment, the therapeutic peptide T specific immune therapy is the combination of 10 peptides (called herein OSE-2101) comprising (or consisting in) the following peptides RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), YLSGADLNL (SEQ ID No 9), aKXVAAWTLKAAa (SEQ ID No 10, with X and a respectively indicating cyclohexylalanine and d-alanine.

More specifically, said treatment comprises a priming period consisting in two to three administrations of the peptide T specific cancer immunotherapy, thereby inducing a central memory T cell response. More preferably, the treatment comprises a priming period consisting in three administrations of the therapeutic peptide T specific immune therapy. In a particular embodiment, in the priming period, the therapeutic peptide T specific immune therapy is administered every one-four weeks, preferably every two-three weeks, more preferably every 3 weeks.

Optionally, in the treatment, the priming period is followed by a maintenance period during which the administration of the therapeutic peptide T specific immune therapy occurs every two-eight months, preferably every two-three months, more preferably every two months through one year and then every three months through one year.

Preferably, the therapeutic peptide T specific immune therapy is administered parentally, preferably subcutaneously.

Preferably, the peptides are emulsified in incomplete Freund's adjuvant or the like, preferably Montanide ISA-51.

Preferably, the doses of peptide are ranging from 0.1 to 10 mg of peptide per injection dose.

Optionally, the total peptide dose for each injection is 5.0 mg.

Preferably, the cancer is a cancer selected from the group consisting of lung cancer such as NSCLC (non-small cell lung cancer) and small cell lung cancer, melanoma, mesothelioma, breast cancers, primary brain cancers, ovarian cancer, uterine carcinoma, especially uterine corpus and/or uterine cervix carcinoma, head and neck cancer, colon or colorectal cancer, gastro-intestinal cancer, renal cancer, sarcoma, germ cell tumors, leukemia, lymphoma, testicular cancers and bladder cancers, preferably selected from the group consisting of NSCLC, colon cancer, breast cancer, ovarian cancer, and a cancer of the head and/or neck, more preferably NSCLC.

The patient is patient HLA-A2 positive patient. Optionally, the patient suffers from an advanced or late-stage cancer. Optionally, the patient suffers from metastases, especially brain metastases. Optionally, the patient has a malignant pleural effusion. Optionally, the patient has already received several lines of treatment prior to the treatment with the therapeutic peptide T specific immune therapy.

Optionally, the treatment is used in combination with a treatment with another antitumor drug and/or with radiotherapy, especially with a checkpoint inhibitor, preferably CTLA-4 and/or PD-1/PD-L1 inhibitor such as pembrolizumab, nivolumab, pidilizumab, BMS936559, MEDI4736, AMP-224, AMP-514, MPDL328OA and avelumab, more particularly in order to transform "non immunogenic T memory" patients into "immunogenic T memory" patients.

DETAILED DESCRIPTION OF THE INVENTION

Previously, only CTL effector cells and HTL effector cells responses were identified following original combination of short peptides epitopes (EP1620456 describing chemical optimization on the binding to the key receptors of T response and original combination of different nature of epitopes) as T cell specific immunotherapy in oncology. Both CTL (Cytotoxic T lymphocytes) and HTL (Helper T lymphocytes) immune responses versus all epitopes were based on effectors T cells after injection of such combination of epitopes from different nature (fixed anchors, heteroclitic and wild type epitope). EP1620456 patent describing the immune response with such original combination was using a standard Elispot measuring effector T cells assay without in vitro expansion in HLA-A2 transgenic models. This standard Elispot assay allows the measurement of T cells capable of immediate secretion of IFN-γ upon antigen/epitope stimulation. These cells mainly represent effector T cells.

The categorization of memory T cells into different subsets (effector memory (TEM) and central memory (TCM)) was studied in several studies exanimating which type of memory cell is capable of providing optimal protection (Jennifer D Bassett et al, 2012, Molecular Therapy, 20, 860-869).

In order to standardize these measures, two Elispot assays allow to separate this 2 main populations: the standard ELISPOT assay quantifies effector memory T cells whereas the cultured ELISPOT assay quantifies expandable memory T cells, representing central memory T cells. Evidence indicates that a different population of T cells, most likely central memory T cells that differentiate into effector T cells during the culture period, are measured by the cultured ELISPOT assay, as compared with the measurement of circulating effector memory T cells that are quantified by the standard ELISPOT (Calarotra S. A. et al supra). This cultured ELISPOT assay is performed by culturing lymphocytes with specific antigens for 10 days allowing T cells to expand in response to the antigen. Then, a standard ELISPOT procedure is applied in response to the corresponding antigens used for the 10-day stimulation period measuring effector function.

Central memory T cells require antigenic re-stimulation to develop effector function. The cultured ELISPOT assay mainly comprises these central memory T cells because the depletion of central-memory T cell population ablated completely responses in cultured Elispot (S. M. Todryk, et al., 2009, Immunology, 128, 83-91). Todryk et al explains the predominant role of central memory T cells in the cultured ELISPOT providing CD4+ and CD8+ specific response. Central memory T cells have a greater capacity than effector memory T cells to persist in vivo and are more efficient in mediating protective immunity because of their increased proliferative capacity.

The invention described below fulfill an unmet need in oncology, providing an optimized administration regimen allowing an early memory T cell response in cancer treatment, preferably an early central memory T cell response, and more particularly an early long term memory T cell response.

More particularly, the present invention relates to a new administration regimen of a short peptide cancer therapy based on multi-epitope T specific cancer immunotherapy. Surprisingly, the inventors have demonstrated that the administration of a short peptide multi-epitopes combination leads to an unexpected strong immune response involving long term memory T cells, in particular central memory T cells. Furthermore, the inventors have also discovered that a very short administration regimen with only three injections is enough to induce this strong and long term response.

Accordingly, the present invention relates to a therapeutic peptide T specific immune therapy as defined herein for use in the treatment of a cancer of an HLA-A2 (Human Leukocyte Antigen A2) positive patient, wherein said treatment comprises a priming period consisting in two to three administrations of said therapeutic peptide T specific immune therapy. It also relates to a method of treatment of a cancer of an HLA-A2 (Human Leukocyte Antigen A2) positive patient in need thereof comprising a priming period consisting in two to three administrations of said therapeutic peptide T specific immune therapy OSE2101 as defined herein. Finally, the present invention relates to the use of a therapeutic peptide T specific immune therapy OSE2101 as defined herein for the manufacture of a cancer treatment, wherein the therapeutic peptide T specific immune therapy is to be administered two to three times during the priming period.

Definitions

An "epitope" is the collective features of a molecule, such as primary, secondary and tertiary peptide structure, and charge, that together form a site recognized by an immunoglobulin, T cell receptor or HLA molecule. Alternatively, an epitope can be defined as a set of amino acid residues which is involved in recognition by a particular immunoglobulin, or in the context of T cells, those residues necessary for recognition by T cell receptor proteins and/or Major Histocompatibility Complex (MHC) receptors. Epitopes are present in nature, and can be isolated, purified or otherwise prepared or derived by humans. For example, epitopes can be prepared by isolation from a natural source, or they can be synthesized in accordance with standard protocols in the art. Throughout this disclosure, epitopes may be referred in some cases as peptides or peptide epitopes.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994). HLA molecules are grouped on the basis of shared peptide-binding specificities. For example, HLA-A2 is a particular type of HLA molecules which share similar binding affinity for peptides bearing certain amino acid motifs. The methods for determining the HLA-A2 status in a patient are well-known and easy to obtain (i.e.; serological samples) by the one skilled in the art.

A "peptide epitope" is a peptide that comprises an allele-specific motif or supermotif such that the peptide will bind an HLA molecule and induce a CTL and/or HTL response. Thus, peptide epitopes of the invention are capable of binding to an appropriate HLA-A2 molecule and thereafter inducing a cytotoxic T lymphocyte (CTL) response, or a helper T lymphocyte (HTL) response, to the peptide.

A "PanDR peptide" or "PADRE®" peptide is a member of a family of molecules that binds more than one HLA class II molecule. The pattern that defines the PADRE® family of molecules can be referred to as an HLA Class II supermotif. A PADRE® molecule binds to HLA class II molecules and stimulates in vitro and in vivo human HTL responses. PADRE peptides are described in the patent EP735893.

A "CTL and/or an HTL response" is a protective or therapeutic immune response to an antigen derived from a pathogenic antigen (e.g., an antigen from an infectious agent or a tumor antigen), which in some way prevents or at least partially arrests disease symptoms, side effects or progression. The immune response may also include an antibody response which has been facilitated by the stimulation of helper T cells.

As used herein, the term "memory T cell" is intended to include both the CCR7– (effector memory T cells) and CCR7+ (central memory T cells) subpopulations of T cells. This definition also includes both class II-restricted CD4 memory T cells and class I-restricted CD8 memory T cells.

The staging of a cancer describes the severity of a person's cancer based on the size and/or extent (reach) of the original (primary) tumor and whether or not cancer has spread in the body (metastasis). NSCLC stages are numbered from 0 to IV. Stages IIIb and IV are the most advanced stages.

"ECOG (Eastern Cooperative Oncology Group) Performance Status" are used by doctors and researchers to assess how a patient's disease is progressing and assess how the disease affects the daily living abilities of the patient. ECOG Performance Status are numbered from 0 to 5. A performance status of 0 match to patients who are fully active and able to carry on all pre-disease performance without restriction. A performance status of 1 match to patients who are restricted in physically strenuous activity but ambulatory and able to carry out work of a light or sedentary nature, e.g., light house work, office work.

The term "overall survival" (OS) refers to the length of time from the date of the start of treatment that patients are still alive. In a clinical trial, measuring the overall survival is one way to see how well a new treatment works.

Therapeutic Peptide T Specific Immunotherapy or Peptide Vaccine

The Multi-epitopes T specific cancer immunotherapy of the invention is able to help the immune system to develop immune memory that can have long-lasting, tumor-specific effects.

An effective peptide T specific cancer immunotherapy requires induction of a wide breadth of CTL specificities. This can be best achieved with optimized epitopes targeting multiple Tumor Associated Antigens (TAAs) as a multi-epitopes combination targeting at least 5 tumor antigens and based on epitopes combination. Preferably, the at least 5 tumor antigens include or are selected among HER2/neu, CEA, MAGE2, MAGE3 and p53.

The Multi-epitopes T specific cancer immunotherapy comprises a combination of epitopes that can be wild-type epitopes and modified epitopes (heteroclitic and fixed anchors epitopes). Preferably, the Multi-epitopes T specific cancer immunotherapy comprises at least 5 epitopes. In a preferred embodiment, the combination of epitopes comprises at least 5 epitopes chosen among those disclosed in Table 6 of the US application US2014/01474790 (incorporated herein by reference). More preferably, the Multi-epitopes T specific cancer immunotherapy comprises at least 5 epitopes allowing to target the combination of the following 5 tumor antigens: HER2/neu, CEA, MAGE2, MAGE3 and p53. For instance, Multi-epitopes T specific cancer immunotherapy may comprise at least 5, 6, 7, 8 or 9 epitopes chosen among those disclosed in Table 6 of the US application US2014/01474790.

The original combination used here (OSE-2101) is made by wild-type epitopes and modified epitopes (heteroclitic and fixed anchors epitopes). More detailed information on heteroclitic and fixed anchors epitopes can be found for instance in the patent EP1620456.

OSE-2101 is a multi-epitope T specific cancer immunotherapy composed of 10 synthetic peptides. Nine of the peptides have been designed to induce a CTL response against TAAs. More particularly, the T specific immune therapy is designed for administration to patients for the induction of CTL directed against carcinoembryonic antigen (CEA), p53, human epidermal receptor-2/neurological (HER-2/neu) and melanoma antigen 2 and 3 (MAGE-2/3). These TAAs have been chosen based on epidemiology because they are frequently over-expressed in various advanced cancers as colon cancers, ovarian cancers, breast cancers and NSCLC. Each CTL epitope is restricted by HLA-A2 superfamily of major histocompatibility complex class I molecules, thereby providing coverage of approximately 45% of the general population. The tenth synthetic peptide is the pan-DR epitope (PADRE), a rationally designed helper T-lymphocyte (HTL) epitope included only to increase the magnitude of CTL responses.

OSE-2101 composition comprises or consists of the following peptides:
RLLQETELV SEQ ID No 1
YLQLVFGIEV SEQ ID No 2
LLTFWNPPV SEQ ID No 3
KVFGSLAFV SEQ ID No 4
KLBPVQLWV SEQ ID No 5, with B indicating α-aminoisobutyric acid
SMPPPGTRV SEQ ID No 6
IMIGHLVGV SEQ ID No 7
KVAEIVHFL SEQ ID No 8
YLSGADLNL SEQ ID No 9
aKXVAAWTLKAAa SEQ ID No 10, with X and a respectively indicating cyclohexylalanine and d-alanine.

Therefore, the therapeutic peptide T specific immune therapy comprises the peptide aKXVAAWTLKAAa (SEQ ID No 10, with X and a respectively indicating cyclohexylalanine and d-alanine) and at least 4, 5, 6, 7, 8 or 9 peptides selected from the group consisting of RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), and YLSGADLNL (SEQ ID No 9).

The peptides can be synthesized using standard Boc or Fmoc chemistry for solid phase peptide synthesis starting with the appropriate resin, and purified by standard methods. Alternatively, the peptide may be produced by genetic engineering with recombinant cells or by RNA, for instance by in vitro translation system.

The Multi-epitope T specific cancer immunotherapy composition may comprise a pharmaceutically acceptable carrier or excipient. More preferably, the pharmaceutically acceptable carrier is an aqueous carrier, especially a buffer. In particular, it may comprise one or several adjuvants. For instance, adjuvants can be incomplete Freund's adjuvant, mineral oil adjuvant, aluminum hydroxide, or alum, GM-CSF. Other suitable adjuvants are well-known in the art.

In one embodiment, the Multi-epitope T specific cancer immunotherapy may comprise peptide pulsed antigen presenting cells, such as dendritic cells.

Preferably, in the Multi-epitope T specific cancer immunotherapy, the peptides are emulsified in incomplete Freund's adjuvant or the like. In a preferred embodiment, the adjuvant is a mineral oil adjuvant, similar to Incomplete Freund's Adjuvant, manufactured and supplied by Seppic SA, Paris, FRANCE. In a most preferred embodiment, the adjuvant is Montanide® ISA 51.

Each peptide of the composition can be present at a concentration of 0.1 mg/ml to 1 mg/ml, preferably 0.5 mg/ml. Preferably, all the peptides are present in the composition at the same concentration.

Preferably, Multi-epitope T specific cancer immunotherapy composition is a sterile, preservative-free emulsion of the 10 peptides at a concentration of 0.5 mg/ml each, formulated in Montanide® ISA 51 adjuvant at a ratio of 1:1 (w:w) and filled into rubber-stoppered glass vials, and refrigerated at 2° to 8° C.

OSE-2101 is manufactured under aseptic conditions. Peptides are dissolved in three different solvents, sterile filtered, pooled and then emulsified in adjuvant via homogenization under controlled conditions. Product release testing included appearance, endotoxin, sterility, viscosity, particle size, peptide concentration of each peptide, volume, pH and potency. Preparation of OSE-2101 composition is detailed in WO2004/094454, FIG. 3A and pages 105-106, the disclosure of which being incorporated herein by reference.

Optionally, in addition to the 10 peptides of OSE-2101, the peptide composition of the present invention may further comprise additional peptides, in particular peptide epitopes used for inducing of cytotoxic T-lymphocyte (CTL) responses and targeting TAAs. For instance, the peptide composition of the present invention may further comprise a peptide as disclosed in WO2009/143843 (the disclosure of which being incorporated herein by reference), and more particularly IDO5 (SEQ ID No 11).

Administration Regimen of the Therapeutic Peptide T Specific Immunotherapy:

The administration regimen of a vaccine comprises a priming period and optionally a maintenance period.

The term "priming period" refers to the period of the vaccination process during which a central memory T cell response is induced against one or several peptides of the therapeutic peptide T specific immunotherapy.

The term "maintenance period" or "boosting period" refers to the period of the vaccination process following the priming period during which the same therapeutic peptide T specific immunotherapy is administered and the T memory immune response is sustained or enhanced. According to a preferred aspect of the present invention, the priming period of a subject under treatment with therapeutic peptide T specific immunotherapy consists in one to three administrations of the therapeutic peptide T specific immunotherapy or vaccine.

In an even more preferred embodiment, the priming period consists in three administrations of the therapeutic peptide T specific immunotherapy or vaccine.

During this priming period, the therapeutic peptide T specific immune therapy is administered every one-four weeks, preferably every two-three weeks, more preferably every 3 weeks.

The priming period is efficient for inducing a central memory T cell response against one or several peptides of the therapeutic peptide T specific immunotherapy, preferably against at least 2, 3, 4 or 5 peptides of the therapeutic peptide T specific immunotherapy.

During the optional maintenance period, which follows the priming period, one or several administrations of the therapeutic peptide T specific immunotherapy or vaccine are realized. During this maintenance period, the administration of the vaccine occurs every two-eight months, preferably every two-three months, for instance every two month through one or two years and then every three months through one or two years.

In an alternative embodiment, the priming period is not followed by a maintenance period.

The priming period and the maintenance period can be separated by a rest period which does not include any the therapeutic peptide T specific immunotherapy administration. This rest period can last four to twelve weeks.

In another alternative embodiment, the priming period is followed by a treatment with a checkpoint inhibitor as the T memory cells induced by the therapeutic peptide T specific immunotherapy are rendered immunogenic the tumor environment.

The present invention further relates to a method for treating cancer in an HLA-A2 positive patient, comprising administering a therapeutic effective amount of therapeutic peptide T specific immunotherapy as disclosed herein, wherein said treatment comprise a priming period during which one to three administrations of said peptide vaccine are performed. The method may further comprise a preliminary step of determining the HLA status of the patient, selecting the HLA-A2 positive patients and administering a therapeutic effective amount of the therapeutic peptide T specific immunotherapy as disclosed herein to the HLA-A2 positive patients. The method may further comprise a maintenance period as defined above. Preferably, the therapeutic peptide T specific immunotherapy is OSE2101.

Dosage

Within the context of the invention, the term "treatment" or "treating" denotes curative, symptomatic, and preventive treatment. Pharmaceutical compositions and preparations of the invention can be used in humans with existing cancer or tumor, preferably at late stages of progression of the cancer. The pharmaceutical compositions and preparations of the invention will not necessarily cure the patient who has the cancer but will delay or slow the progression or prevent further progression of the disease, ameliorating thereby the patient's condition. In particular, the pharmaceutical compositions and preparations of the invention reduce the development of tumors, and/or prevent metastasis occurrence or development and cancer relapse. In treating the cancer, the pharmaceutical composition of the invention is administered in a therapeutically effective amount.

By "effective amount" it is meant the quantity of the pharmaceutical composition of the invention which prevents, removes or reduces the deleterious effects of brain metastases. It is understood that the administered dose may be adapted by those skilled in the art according to the patient, the pathology, the mode of administration, etc. The dosage and regimen depends on the stage and severity of the disease to be treated, the weight and general state of health of the patient and the judgment of the prescribing physician. More particularly, by "therapeutically efficient amount of the therapeutic peptide T specific immunotherapy as disclosed herein" is intended the amount which is sufficient to increase the overall survival of a patient. In particular, by "therapeutically efficient amount of the therapeutic peptide T specific immunotherapy as disclosed herein" is intended the amount which is sufficient to induce a central memory T cell response against one or several peptides of the therapeutic peptide T specific immunotherapy.

Previous cancer trials have tested escalating doses of peptide, ranging from 0.1 to 10 mg of peptide per injection dose, emulsified in incomplete Freund's adjuvant. At all doses tested, the peptide/incomplete Freund's adjuvant treatment was deemed to be safe and well tolerated, with no severe dose-related systemic toxicities being reported.

therapeutic peptide T specific immunotherapy as disclosed herein can be administered by any appropriate route, in particular by parenteral route such as subcutaneous, intradermal or intramuscular route or by aerosol, transmucosal, intrapleural, or intrathecal routes. In a most preferred embodiment, the peptides composition is administered subcutaneously. Preferably, the therapeutic peptide T specific immunotherapy as disclosed herein is designed for subcutaneous injection.

Preferably, the doses of peptide are ranging from 0.1 to 10 mg of peptide per injection dose. In a preferred embodiment, the total peptide dose for each injection or administration will be 5.0 mg (1 mL of drug product containing 0.5 mg of each peptide).

Cancer

According to a preferred aspect of the present invention, subjects of vaccination with OSE-2101 composition are patients with a cancer. In a preferred embodiment, patient's cancer are due to one of the following cancers: lung cancer such as NSCLC (non-small cell lung cancer) and small cell lung cancer, melanoma, mesothelioma, breast cancers, primary brain cancers, ovarian, uterine carcinoma, especially uterine corpus and/or uterine cervix carcinoma, head and neck, colon, gastro-intestinal, renal cancers, sarcoma, germ cell tumors, leukemia, lymphoma, testicular cancers and bladder cancers, preferably NSCLC, colon cancer, breast cancer, ovarian cancer, and a cancer of the head and/or neck, more preferably NSCLC.

In another preferred embodiment, patient's cancer are advanced cancer. The term "advanced cancer" refers to a cancer at an advanced stage of development, i.e. a cancer that has spread in the body (metastasis). Preferably, the patient suffers from brain metastases.

Alternatively, the patient has a malignant pleural effusion, preferably a metastatic pleural effusion, in particular associated with lung cancer, breast cancer, lymphoma or leukemia.

Optionally, the patient has already received several lines of treatment prior to the vaccination by the peptide composition. In a particular embodiment, the patient has a positive HTL response.

Combination with Another Antitumor Drug.

Optionally, the treatment is used in combination with a treatment with another antitumor drug, in particular a chemotherapy, hormonotherapy and/or immunotherapy.

For instance, the chemotherapy can be selected among cisplatin, carboplatin, cyclophosphamide, etoposide, teniposide, mitomycin, irinotecan, vinorelbine, etoposide, ifosfamide, temozolomide, fluorouracil (5FU), docetaxel, pemetrexed, navelbine, drugs that target tumor blood vessel growth (VEGF) such as bevacizumab, ramucirumab; prednisone; tyrosine kinase inhibitors targeting EGFR such as gefitinib, erlotinib, afatinib; ALK inhibitors such as crizotinib; ceritinib and any combination thereof.

In a preferred embodiment, the vaccine treatment of the present invention is used in combination with a checkpoint inhibitor, especially a CTLA-4 inhibitor and/or a PD-1 or PD-L1 inhibitor; IDO inhibitors. The treatment with the checkpoint inhibitor can be performed before, simultaneously or after the treatment with the therapeutic peptide T specific immunotherapy as disclosed herein, in particular the priming period of the treatment.

The present invention relates to a kit or product comprising (a) the therapeutic effective amount of therapeutic peptide T specific immunotherapy as disclosed herein; and (b) a check point inhibitor, preferably a CTLA-4 inhibitor and/or PD-1 or PD-L1 inhibitor, as a combined preparation for simultaneous, separate or sequential use, in particular in the treatment of cancer.

Preferably, the therapeutic peptide T specific immunotherapy is OSE-2101.

In a preferred embodiment, the treatment with a checkpoint inhibitor is performed after the priming period of the treatment with the therapeutic effective amount of therapeutic peptide T specific immunotherapy as disclosed herein.

Several PD-1/PD-L1 inhibitors are already available or under clinical development. For instance, the PD-1/PD-L1 inhibitors can be chosen among the non-exhaustive list including pembrolizumab (Merk), nivolumab (Bristol Myers Squibb), pidilizumab (Cure Tech), BMS936559 (Bristol Myers Squibb), MEDI4736 (Astra Zeneca), AMP-224 (Astra Zeneca), AMP-514 (Astra Zeneca), MPDL328OA (Roche), avelumab (also known as MSB0010718C from Merck KgA Serono/Pfizer). For instance, the PD-1/PD-L1 inhibitors can be chosen among those disclosed in WO2013/079174.

For instance, the CTLA-4 inhibitors can be chosen among the non-exhaustive list including Tremelimumab (Pfizer Medimmune) and ipilimumab (BMS).

Further aspects and advantages of this invention will be disclosed in the following experimental section, which should be regarded as illustrative and not limiting the scope of this application.

EXAMPLES

Example 1

Figure 1:
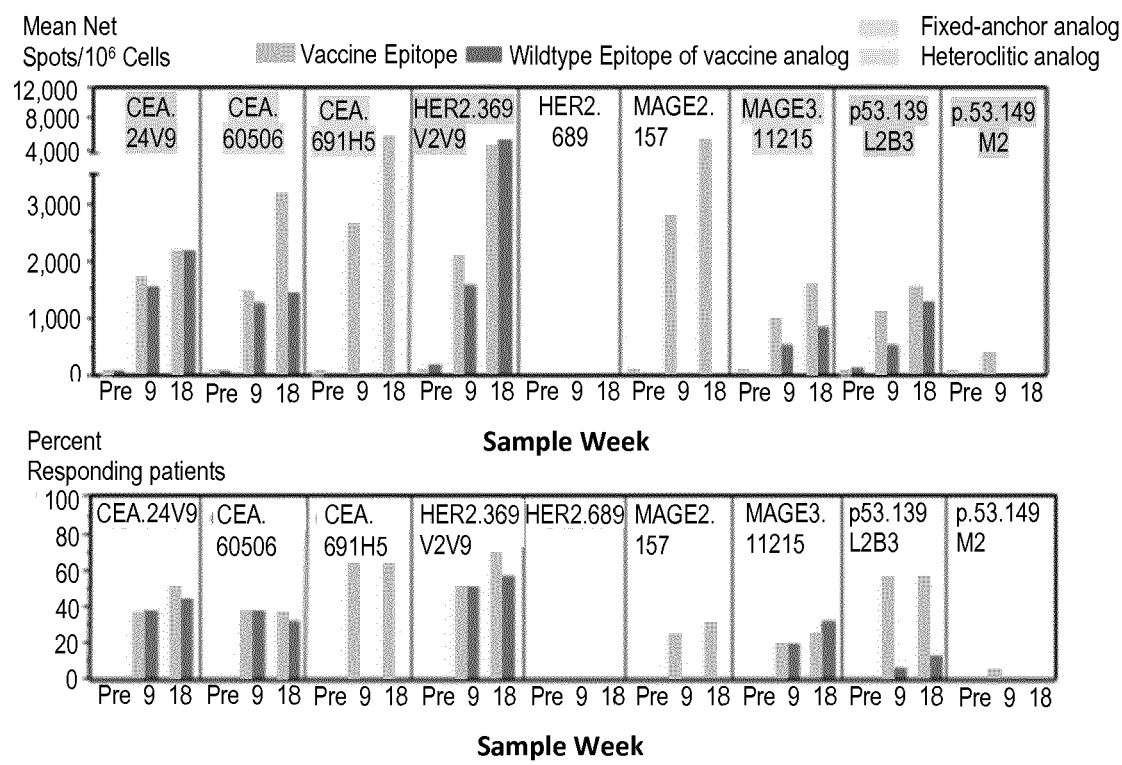
FIG. 1: Phase 1/2 W9 W18 magnitude of central memory T cell responses induced by OSE2101.

Early Immune Response Though Central Memory T Cells Involvement

In the Phase 1/2 clinical studies, the safety and immunogenicity of a 10-peptide enhanced epitope combination, OSE-2101, rationally designed to induce broad multi-epitope CTL responses in early stage colon and NSCLC patients. In addition to multi-epitope coverage, OSE-2101 also targeted epitopes from five Tumor antigens which are widely expressed on breast, colon and non-small cell lung, ovarian, tumors (CEA, HER-2/neu, p53, MAGE2 and MAGE3) making this product suitable for therapy against different cancer indications. As a source of T-cell helper for CTL induction, the universal HTL epitope Pan DR Epitope was also included and a mineral oil adjuvant was used for the final formulation of this T specific cancer immunotherapy.

Patient eligibility criteria. OSE-2101 was tested in two disease-specific phase I clinical trials enrolling HLA-A2+ patients with histologically confirmed stage IIB/IIIA NSCLC or stage III colon cancer. All patients were diagnosed as NED within the past 6 months after undergoing standard therapy. Patients met normal laboratory parameters for blood chemistry and white cell counts and had an Eastern Cooperative Oncology Group performance status of 0 or 1. They were excluded if treated with immunomodulatory agents within one month of study entry or with other cancer immunotherapies. Patients with a history of other cancers, except basal or squamous cell carcinoma of the skin or in situ cervical cancer, were also excluded as were patients with concurrent acute medical conditions or specified autoimmune diseases.

Peptides. The immunogenicity of all immune monitoring epitopes was confirmed by stimulating CTL induced by treatment of HLA-A2.1/$K^b$ transgenic mice with a preclinical lot of OSE-2101 (standard Elispot assay).

Clinical study design. Both trials were designed as phase 1/2, open label, multi-center, single dose, multiple administration studies to evaluate the safety and immunogenicity of the OSE-2101 immunotherapy. Patients were treated with 1 ml OSE-2101 every 3 weeks for a total of six doses. Each dose was administered subcutaneously in the same vicinity in the deltoid or upper thigh region, or at a contralateral site if local side-effects were observed. The study duration for each completed patient was 18 weeks. Clinical responses or patient survival were not measured in either phase 1/2 studies.

Clinical sample processing. Blood or leukapheresis product was obtained from patients at the pre-treatment, the Week 9 and Week 18 time points, 3 weeks after the third and sixth dose of OSE-2101 respectively. Peripheral blood mononuclear cells (PBMC) were isolated from samples within 24 hours of collection using a FICOLL-PAQUE density gradient and cryopreserved in containers designed to ensure optimal freezing (Mr. Frosty, Nalgene). For use, cells were rapidly thawed at 37° C. then transferred to human AB serum-containing medium for work-up.

Measurement of central T memory cells responses and T effector memory cells. The CTL responses in 16 total patients (10 colon and six NSCLC) were monitored for CTL responses against each epitope and against the wild-type epitope of epitopes analogs. For each patient, the pre-treatment, Week 9 and Week 18 time points were batch-tested in the same experiment to allow pre- versus post-treatment response comparison in the same experiment. Central T memory cells responses were measured using an IFN-γ enzyme-linked immunospot (cultured ELISPOT) assay following in vitro stimulation of PBMC for 10 days with each vaccine epitope. Briefly, PBMC from each time point were stimulated on day 0 with 10 µg/ml of each epitope individually in replicate in 48-well culture plates ($2\times10^6$ PBMC/well). All cultures were fed with rIL-2 (Endogen, Woburn, Mass.; 10 U/ml final concentration) on days 1, 4 and 7. Ten days after initiation of culture, cells were harvested and tested for activity against specific vaccine peptides and corresponding wild-type peptides of vaccine analogs in the T memory ELISPOT assay. Cells were tested in Millipore IP 96-well plates pre-coated with mouse anti-human IFN-γ antibody (Mabtech USA, Cincinnati, Ohio). Five$\times10^4$ cells and $1.25\times10^4$ cells from each culture were plated in triplicate wells together with $10^5$ irradiated autologous PBMC and 10 µg/ml peptide. As a control, CTL were also tested against an irrelevant HLA-A2.1-binding HBV peptide. After 20 hours incubation, T memory ELISPOT plates were developed by performing sequential incubations with biotinylated anti-human IFN-γ antibody (Mabtech USA), Avidin-Peroxidase Complex (APC, Vector Laboratories, Burlingame, Calif.), and 3-amino-9-ethyl carbazole (AEC) substrate (Sigma Aldrich, St. Louis, Mo.). Spot-forming cells (SFC) were enumerated using a computer-assisted image analysis system (Zeiss KS ELISPOT Reader, Carl Zeiss MicroImaging, Thornwood, N.J.). Data is reported as the net SFC per $5\times10^4$ cells after subtracting spots induced with the irrelevant HBV peptide.

The central T memory cultured ELISPOT assay was qualified using HLA-A2+ PBMC from patients who demonstrated a recall T effector memory response against an EBV BMLF1 CTL epitope (sequence, GLCTLVAML, SEQ ID NO: 12) under identical stimulation conditions used for testing clinical samples. Specific response generated from these donors were titrated at limiting cell doses and a linear response was measured (correlation coefficient=0.99). The lower detection limit of the assay was determined to be 5 SFC/well and the upper limit was 600 SFC. The inter-experiment reproducibility was evaluated by repeated testing of cryopreserved pre-vaccination PBMC samples from positive donors on separate days, and the coefficient of variation (CV) ranged from 7-12% in these assays. To assess inter-operator reproducibility, two operators tested pre-treatment PBMC from the same patient on different days and the CV was 13-16% at the optimal cell dose. The CV values were considered to be within an acceptable range of variability and strongly supported the use of our assay for analyses of clinical immune responses.

Response criteria. Positive response criteria were established prospectively after analyzing the variability of pre-treatment responses against each epitope and the irrelevant HBV control epitope. The mean SFC response in a post-treatment sample was considered a positive epitope-induced T memory cell response if it met all of the following: 1) was greater than 5 SFC above the irrelevant epitope response, 2) was greater than the mean SFC of the irrelevant epitope response, plus 2 SD, and 3) was two-fold greater than the SFC response in the pre-treatment sample from the same patient, plus 2 SD. The inclusion of "plus two standard deviations" was used to accommodate the assay variability and served to make the criteria more stringent.

Results

Patient characterization. Fourteen patients with stage III colon cancer enrolled in the trial and ten patients completed the study after receiving six doses of OSE-2101. In the NSCLC trial ten patients with stage IIB/IIIA disease were enrolled and six patients completed the study. OSE-2101 was deemed safe and tolerated by patients in the two clinical trials with typical side-effects common to peptides prepared in mineral oil adjuvant being observed.

Immunogenicity of OSE-2101 A total of 16 patients (10 colon cancer and 6 NSCLC) receiving the full course of six OSE-2101 doses were evaluated for the frequency, breadth and magnitude of TAA-specific central T memory cell responses induced by the specific immunotherapy. To improve detection of central memory T cell responses PBMC were stimulated in vitro for 10 days with each epitope. The effector activity of the in vitro expanded PBMC was measured with an IFN-γ ELISPOT assay against the respective epitope and an irrelevant HLA-A*0201-binding HBV epitope. If the epitope was an analog the corresponding wild-type epitope was also tested.

Results from immune monitoring of the 16 patients indicated that OSE-2101 was capable of inducing a wide breadth of central memory T cell responses in patients. In the colon cancer trial, eight of the 10 patients surprisingly generated CTL responses against four or more vaccine epitopes at the Week 9 and/or Week 18 time points (FIG. 1). The average magnitude of the cultured ELISPOT was in the same range between Week 9 and Week 18.

Patient 607 demonstrated the widest breadth and highest magnitude of central T cell memory responses, displaying responses between 60-200 SFC per $5 \times 10^4$ cells against seven epitopes at the Week 9 time point. More importantly, five of the seven induced T memory responses in this patient were directed against wild-type epitopes. At the Week 18 time point, patient 607 generated central memory T cell responses, some exceeding 1000 SFC, against six of the same epitopes at Week 9.

Equally noteworthy were the multi-epitope responses observed in colon cancer patients 601, 603, 604 and 606 to five or more epitopes surprisingly at the Week 9 and/or also at Week 18 time points.

Multi-epitope central memory T cell responses were also observed in NSCLC patients, surprisingly at the Week 9 and/or also at Week 18 time points. All of the data described utilized a testing protocol where PBMC samples were cultured in vitro for 10 days with individual OSE-2101 epitopes to expand in vivo-primed CTL prior to testing in the ELISPOT assay and the measure central memory T cell response and the in vitro stimulation step as cultured Elispot was required to see responses to epitopes.

Immunogenicity of different epitope classes. Analysis of the frequency and magnitude of CTL responses indicated that most of the epitopes and all of the epitope classes represented in the product were immunogenic in patients. Overall, eight of the nine vaccine epitopes induced central memory T cell responses in at least one colon cancer patient and six vaccine epitopes were immunogenic in at least one NSCLC patient. Three of the fixed-anchor analogs (CEA.24V9 (SEQ ID No 3), HER2.369V2V9 (SEQ ID No 4) and p53.139L2B3 (SEQ ID No 5)) and two heteroclitic analogs (CEA.691H5 (SEQ ID No 7) and CEA.605D6 (SEQ ID No 9)) were particularly immunogenic as 60-80% of colon cancer patients and 40-80% of the HLA-A*0201-typed NSCLC patients responded to each of the analogs (Table 1A and 1B week 9 or week 18 responses). The heightened immunogenicity of the analogs was also indicated by average response magnitudes ranging from 70-180 SFC at Week 9 and from 90-315 SFC at Week 18 in colon cancer patients (Table 1A) and 60-138 SFC at Week 18 in NSCLC patients (Table 1B).

Immunological testing of the 16 colon and NSCLC patients who completed treatment indicated that OSE-2101 was successful in inducing a wide breadth of CTL and memory T cell responses in individual patients as soon as after 3 injections, characterized by the simultaneous induction of CTL specificities directed against several epitopes. The broad CTL/though central memory T cell responses observed in individual patients in both cohorts indicated the potential long term efficacy for immunotherapy in early and late stage patients. Instead, simultaneous CTL and central Memory T cell responses is addressing a long term clinical benefit of the multi-epitope approach to cancer immunotherapy.

TABLE 1A

A. Summary of CTL responses in 10 colon patients

| Patient | Sample | CEA.24V9 | | CEA.605D6 | | CEA.691H5 | | HER2.369L2V9 | | MAGE2.157 |
| --- | --- | --- | --- | --- | --- | --- | --- | --- | --- | --- |
| | | A[a)] | WT[b)] | A | WT | A | WT | A | WT | WT |
| 551 | Pre-vacc | 9.3[c)] | 18.6 | 15.6 | 0.8 | 0.0 | 0.0 | 28.7 | 1.8 | 1.3 |
| | Week 9 | 42.7[d)] | —[e)] | — | — | 92.7 | — | 134.7 | 119.7 | — |
| | Week 18 | — | — | — | — | 68.7 | — | 80.7 | 22.7 | 45.7 |
| 601 | Pre-vacc | 0.0 | 0.5 | 0.0 | 3.0 | 0.0 | 1.3 | 0.0 | 0.7 | 0.0 |
| | Week 9 | 118.0 | 92.3 | 88.3 | 74.3 | 417.3 | — | 112.7 | 102.0 | — |
| | Week 18 | 96.0 | 55.0 | — | — | 133.7 | — | 52.3 | 55.7 | — |
| 602 | Pre-vacc | 0.0 | 0.0 | 8.5 | 3.8 | 0.0 | 1.0 | 0.0 | 3.3 | 0.0 |
| | Week 9 | — | — | — | — | — | — | — | — | — |
| | Week 18 | — | — | — | — | — | — | — | — | — |

TABLE 1A-continued

A. Summary of CTL responses in 10 colon patients

| Patient | Sample | | | | | | | | | |
|---|---|---|---|---|---|---|---|---|---|---|
| 603 | Pre-vacc | 0.0 | 0.5 | 6.0 | 1.0 | 0.0 | 0.7 | 6.3 | 0.0 | 0.3 |
| | Week 9 | 63.0 | 60.3 | 114.7 | 101.0 | 32.7 | — | 30.0 | 26.3 | 320.0 |
| | Week 18 | 20.7 | 32.7 | — | — | 8.0 | — | — | 11.3 | — |
| 604 | Pre-vacc | 0.0 | 0.0 | 0.0 | 0.0 | 0.0 | 0.0 | 0.0 | 0.0 | 3.0 |
| | Week 9 | 55.3 | 75.0 | 70.0 | 62.3 | 109.3 | — | 88.3 | 66.3 | — |
| | Week 18 | 187.0 | 161.3 | 413.3 | — | 397.3 | — | 314.7 | 220.0 | — |
| 605 | Pre-vacc | 0.0 | 3.9 | 0.0 | 0.0 | 5.0 | 13.7 | 0.0 | 0.0 | 20.3 |
| | Week 9 | 43.7 | 30.0 | — | — | 65.7 | — | 32.7 | 35.0 | — |
| | Week 18 | 109.7 | 129.7 | — | — | — | — | 33.7 | — | — |
| 606 | Pre-vacc | 3.0 | 1.3 | 5.2 | 0.0 | 2.0 | 1.2 | 3.7 | 5.7 | 3.7 |
| | Week 9 | — | — | — | — | 24.3 | — | — | — | — |
| | Week 18 | — | — | — | — | 45.0 | — | 71.0 | 38.3 | 24.7 |
| 607 | Pre-vacc | 4.2 | 1.7 | 2.7 | 0.0 | 0.0 | 0.0 | 3.3 | 2.2 | 0.7 |
| | Week 9 | 196.7 | 165.7 | 72.7 | 30.3 | 593.3 | — | 389.3 | 176.7 | 172.0 |
| | Week 18 | 586.7 | 426.7 | 414.7 | 372.0 | 1648.0 | — | 1642.7 | 1658.7 | 1184.0 |
| 608 | Pre-vacc | 8.5 | 0.0 | 4.3 | 0.0 | 3.7 | 0.5 | 0.0 | 2.0 | 1.8 |
| | Week 9 | — | — | — | 6.3 | — | — | — | — | — |
| | Week 18 | — | — | — | — | 18.0 | — | — | — | — |
| 609 | Pre-vacc | 3.7 | 4.5 | 6.2 | 0.5 | 0.0 | 0.0 | 1.5 | 2.0 | 6.8 |
| | Week 9 | — | 28.3 | 75.3 | 100.7 | 89.0 | — | 58.0 | 24.7 | — |
| | Week 18 | 31.7 | 29.0 | 22.0 | 17.0 | 86.0 | — | 14.7 | 9.3 | — |
| Mean SFC | Week 9 | 86.5 | 75.3 | 84.2 | 62.5 | 178.0 | — | 120.8 | 78.7 | 246.0 |
| | Week 18 | 172.0 | 139.1 | 283.3 | 194.5 | 300.6 | — | 315.7 | 288.0 | 418.1 |

| | | MAGE3.112I5 | | p53.139L2B3 | | p53.149M2 | | No. Positive Epitopes | |
| --- | --- | --- | --- | --- | --- | --- | --- | --- | --- |
| Patient | Sample | A | WT | A | WT | A | WT | Vaccine | WT[f] |
| 551 | Pre-vacc | 10 | 17 | 13.5 | 12.8 | 0.0 | 2.7 | | |
| | Week 9 | — | — | — | — | — | — | 3 | 1 |
| | Week 18 | 8.7 | 7.7 | — | — | — | — | 4 | 3 |
| 601 | Pre-vacc | 0.0 | 1.0 | 0.3 | 2.8 | 0.0 | 0.0 | | |
| | Week 9 | 27.0 | — | 129.0 | — | — | — | 6 | 3 |
| | Week 18 | — | — | 96.0 | — | — | — | 4 | 2 |
| 602 | Pre-vacc | 2.0 | 1.5 | 0.0 | 0.0 | 0.5 | 1.0 | | |
| | Week 9 | — | — | — | — | — | — | 0 | 0 |
| | Week 18 | — | — | 22.7 | — | — | — | 1 | 0 |
| 603 | Pre-vacc | 3.5 | 1.8 | 6.0 | 0.8 | 1.0 | 0.0 | | |
| | Week 9 | — | — | 85.3 | — | — | — | 6 | 4 |
| | Week 18 | 16.0 | 12.3 | — | — | — | — | 3 | 3 |
| 604 | Pre-vacc | 0.0 | 0.0 | 0.0 | 0.0 | 0.2 | 4.5 | | |
| | Week 9 | 60.3 | 43.7 | 41.0 | — | — | — | 6 | 4 |
| | Week 18 | 268.0 | — | 188.7 | — | — | — | 6 | 2 |
| 605 | Pre-vacc | 0.0 | 0.0 | 1.0 | 1.8 | 0.0 | 9.3 | | |
| | Week 9 | — | — | 9.7 | — | — | — | 4 | 2 |
| | Week 18 | — | — | 44.7 | — | — | — | 3 | 1 |
| 606 | Pre-vacc | 0.7 | 1.7 | 0.0 | 0.3 | 0.0 | 1.0 | | |
| | Week 9 | — | — | 43.7 | — | — | — | 2 | 0 |
| | Week 18 | 18.7 | — | 37.7 | — | — | — | 5 | 2 |
| 607 | Pre-vacc | 4.3 | 0.0 | 4.2 | 0.7 | 1.0 | 0.0 | | |
| | Week 9 | 60.3 | 23.0 | 114.3 | — | — | — | 7 | 5 |
| | Week 18 | — | — | 146.7 | — | — | — | 6 | 4 |
| 608 | Pre-vacc | 2.7 | 0.0 | 24.0 | 2.8 | 2.0 | 2.3 | | |
| | Week 9 | — | — | — | — | 18.0 | — | 1 | 1 |
| | Week 18 | — | — | — | — | — | — | 1 | 0 |
| 609 | Pre-vacc | 1.7 | 1.0 | 35.8 | 0.0 | 0.0 | 4.2 | | |
| | Week 9 | — | — | — | — | — | — | 3 | 3 |
| | Week 18 | — | — | — | — | — | — | 4 | 3 |
| Mean SFC | Week 9 | 49.2 | 33.3 | 70.5 | — | 18.0 | — | | |
| | Week 18 | 77.8 | 10.0 | 89.4 | — | — | — | | |

[a] A, CTL were tested against the vaccine analog.
[b] WT, CTL were tested against the vaccine wild type epitope corresponding to the vaccine analog.
[c] Value indicates the net pre-vaccination SFC per 50,000 cells tested against the indicated epitope.
[d] Value indicates the net SFC per 50,000 cells of vaccine positive responses.
[e] —, indicates SFC response did not meet criteria and vaccine response was negative.
[f] Total number of vaccine positive response against a vaccine wild type epitope or the wild type epitope corresponding to the vaccine analog.

TABLE 1B

B. Summary of CTL responses in 6 NSCLC patients

| Patient | Sample | CEA.24V9 A[a] | CEA.24V9 WT[b] | CEA.605D6 A | CEA.605D6 WT | CEA.691H5 A | CEA.691H5 WT | HER2.369L2V9 A | HER2.369L2V9 WT | MAGE2.157 WT |
|---|---|---|---|---|---|---|---|---|---|---|
| 201 | Pre-vacc | 0.0[c] | 0.0 | 0.0 | 0.0 | 0.0 | 0.0 | 0.0 | 0.0 | 32.7 |
|  | Week 9 | — | —[e] | — | — | — | — | — | — | — |
|  | Week 18 | — | — | — | — | — | — | — | — | — |
| 502 | Pre-vacc | 0.0 | 0.0 | 0.0 | 9.3 | 4.2 | 4.0 | 4.7 | 2.2 | 0.7 |
|  | Week 9 | — | — | — | — | — | — | — | — | 9.3 |
|  | Week 18 | — | — | — | — | — | — | — | — | — |
| 504 | Pre-vacc | 0.0 | 0.0 | 3.3 | 0.3 | 0.0 | 0.5 | 1.7 | 1.0 | 1.7 |
|  | Week 9 | — | — | 20.7 | — | 42.7 | — | 84.3 | 71.0 | 50.7 |
|  | Week 18 | 25.3[d] | 23.3 | 214.3 | 15.7 | 284.0 | — | 284.0 | 155.7 | 124.7 |
| 505 | Pre-vacc | 5.2 | 1.5 | 8.8 | 9.7 | 6.7 | 11.7 | 16.7 | 32.0 | 7.5 |
|  | Week 9 | — | — | — | — | — | — | — | — | — |
|  | Week 18 | — | — | 60.7 | 33.0 | 45.3 | — | 53.0 | — | — |
| 532 | Pre-vacc | 0.0 | 0.0 | 0.0 | 0.2 | 0.0 | 0.0 | 0.0 | 0.0 | 0.0 |
|  | Week 9 | — | — | — | — | 125.7 | — | — | — | — |
|  | Week 18 | 43.3 | — | — | — | — | — | 78.3 | — | — |
| 651 | Pre-vacc | 0.2 | 0.7 | 0.0 | 0.0 | 1.7 | 0.2 | 2.3 | 1.2 | 2.0 |
|  | Week 9 | — | — | — | — | — | — | — | — | — |
|  | Week 18 | — | — | — | — | 68.7 | — | 22.0 | — | 9.0 |
| Mean SFC | Week 9 | — | — | 20.7 | — | 84.2 | — | 84.3 | 71.0 | 30.0 |
|  | Week 18 | 34.3 | 23.3 | 137.5 | 24.3 | 132.7 | — | 109.3 | 155.7 | 66.8 |
| No. Positive Responses | Week 9 | 0 | 0 | 1 | 0 | 2 | 0 | 1 | 1 | 2 |
|  | Week 18 | 2 | 1 | 2 | 2 | 3 | 0 | 4 | 1 | 2 |

| Patient | Sample | MAGE3.112I5 A | MAGE3.112I5 WT | p53.139L2B3 A | p53.139L2B3 WT | p53.149M2 A | p53.149M2 WT | No. Positive Epitopes Vaccine | No. Positive Epitopes WT[f] |
|---|---|---|---|---|---|---|---|---|---|
| 201 | Pre-vacc | 22.8 | 51.5 | 0.0 | 0.0 | 16.5 | 16.5 |  |  |
|  | Week 9 | — | — | — | — | — | — | 0 | 0 |
|  | Week 18 | — | — | — | — | — | — | 0 | 0 |
| 502 | Pre-vacc | 3.5 | 2.5 | 0.0 | 0.0 | 5.7 | 6.2 |  |  |
|  | Week 9 | — | — | — | — | — | — | 1 | 1 |
|  | Week 18 | — | — | — | — | — | — | 0 | 0 |
| 504 | Pre-vacc | 1.8 | 0.3 | 1.3 | 1.8 | 1.8 | 0.8 |  |  |
|  | Week 9 | — | — | 18.7 | — | — | — | 5 | 2 |
|  | Week 18 | — | — | 90.3 | — | — | — | 6 | 4 |
| 505 | Pre-vacc | 13.3 | 13.8 | 0.0 | 5.8 | 21.7 | 12.5 |  |  |
|  | Week 9 | — | — | — | — | — | — | 0 | 0 |
|  | Week 18 | — | — | 20.3 | — | — | — | 4 | 1 |
| 532 | Pre-vacc | 0.0 | 7.0 | 25.2 | 0.5 | 2.7 | 0.0 |  |  |
|  | Week 9 | — | — | 53.0 | — | — | — | 2 | 0 |
|  | Week 18 | — | — | 117.3 | — | — | — | 3 | 0 |
| 651 | Pre-vacc | 2.7 | 0.8 | 0.0 | 1.0 | 3.3 | 2.8 |  |  |
|  | Week 9 | — | — | 6.0 | — | — | — | 1 | 0 |
|  | Week 18 | — | — | 20.0 | — | — | — | 4 | 1 |
| Mean SFC | Week 9 | — | — | 25.9 | — | — | — |  |  |
|  | Week 18 | — | — | 62.0 | — | — | — |  |  |
| No. Positive Responses | Week 9 | 0 | 0 | 3 | 0 | 0 | 0 |  |  |
|  | Week 18 | 0 | 0 | 4 | 0 | 0 | 0 |  |  |

[a] A, CTL were tested against the vaccine analog.
[b] WT, CTL were tested against the vaccine wild type epitope corresponding to the vaccine analog.
[c] Value indicates the net pre-vaccination SFC per 50,000 cells tested against the indicated epitope.
[d] Value indicates the net SFC per 50,000 cells of vaccine positive responses.
[e] —, indicates SFC response did not meet criteria and vaccine response was negative.
[f] Total number of vaccine positive response against a vaccine wild type epitope or the wild type epitope corresponding to the vaccine analog.

Example 2

Early T Memory Cell Involvement Confirmed in Phase 2

CTL Immune responses measured though cultured Elispot. The immunogenicity was measured in Phase 2 clinical trial on cryopreserved PBMC from each test sample were thawed in 5% human culture medium (RPMI-1640 medium with 25 mM HEPES, supplemented with 5% human AB serum, 4 mM L-glutamine, 0.5 mM sodium pyruvate, 0.1 mM MEM non-essential amino acids, 100 µg/ml streptomycin, and 100 U/ml penicillin) containing 30 µg/ml DNAase. After centrifugation for 5 minutes at 1200 rpm, the cell pellets were resuspended in 5% human culture medium and washed 2 times. For the central Memory T cell cultured ELISPOT assay, 2×10⁶/ml PBMC were placed in replicate wells in a 48-well plates and stimulated for 10 days with 10 µg/ml of each peptide. As a positive control, PBMC were also stimulated with a pool of recall viral peptides. Human rIL2 (10 U/ml) was added to the peptide-stimulated cultures at day 1, day 4 and day 7. After 10 days the stimulated cells were harvested and plated at a concentration of 5×10⁴/well. Assay wells also received irradiated autologous PBMC (1×10⁵/well) and 10 µg/ml peptide, either the vaccine peptide, irrelevant peptide or positive control peptides. Cells stimulated in vitro with each analog epitope were also tested against the corresponding wild-type epitope.

HTL Immune responses measured though standard Elispot. For the HTL ELISPOT assay measuring T helper responses to the PADRE epitope, 4×106/ml PBMC were placed in a 12 well-plate for overnight culture. Cells were then harvested and placed at 2×105/well in flat-bottom 96-well nitrocellulose plates which had been pre-coated with anti-IFN-γ monoclonal antibody (mAb) (10 µg/ml; clone 1-D1K; Mabtech). Cells plated in 6-well replicates were stimulated with 10 µg/ml PADRE peptide or with an irrelevant malaria SSP2 peptide. After 20 hrs incubation at 37° C., the assay plates were washed with PBS/0.05% Tween-20 and 100 µl/well of biotinylated anti-IFN-γ mAb (2 µg/ml; clone 7-B6-1; Mabtech) was added to wells. The plates were incubated for 2 hrs at 37° C. then washed 6 times. Finally, spots from IFN-γ-secreting cells were developed by sequentially incubating wells with Vectastain ABC and 3-amino-9-ethyl carbazole (AEC) solutions. Spots were counted by a computer-assisted image analysis reader (Zeiss KS ELISPOT Reader).

Data analysis and acceptance criteria. Mean and standard deviation (SD) of spots in replicate wells were calculated in all assays by transferring raw ELISPOT data from each experiment to an Excel-based computer program. Positive vaccine-induced T-cell responses were determined according to the criteria described below.

Acceptance Criteria for peptide-Induced specific T-cell response through central memory T cells: The positive criteria for CTL responses used in the phase 2 trial was identical to the criteria in the phase 1/2 trials which was established prospectively after analyzing the variability of pre-treatment responses in patients against each vaccine epitope and the irrelevant HBV control epitope. A positive peptide-induced CTL/T memory response to a given epitope met all of the following conditions: 1) was greater than 5 SFC above the irrelevant epitope response, 2) was greater than the mean SFC of the irrelevant epitope response, plus 2 SD, and 3) was two-fold greater than the SFC response in the pre-vaccination sample from the same patient, plus 2 SD. The inclusion of "plus two standard deviations" was used to accommodate the assay variability and served to increase the criteria stringency.

The criteria for a positive HTL response to the HTL PADRE epitope, measured without prior expansion of PBMC, were as follows: 1) a PADRE-specific response >5 net SFC per 2×105 cells after subtracting background; 2) for each sample tested in 6-well replicates, a t-test p value<0.05 when comparing SFC from wells stimulated with the irrelevant HLA-DR binding malaria peptide versus wells stimulated with the PADRE peptide; and 3) a t-test p value<0.05 when comparing SFC induced by stimulation with the PADRE peptide in the pre- versus post-vaccination samples. All three criteria had to be fulfilled before a HTL response was considered to be induced by OSE-2101 vaccination.

Results

Patient enrollment and immune monitoring criteria. A total of 64 HLA-A2+ patients with stage IIIB, IV or recurrent NSCLC in the phase 2 trial were treated with at least one dose of OSE-2101. Thirty three patients completed the initial phase of the study consisting of six doses of OSE-2101 administered at 3-week intervals and were monitored for epitopes-induced T-cell/T memory cells responses. Results of tests from this patient cohort are described below with a particular attention on early response at W9 (after 3 injections) and W18 (after 6 injections).

The breadth of CTL/central memory T cell responses induced in each of the 11 first patients and the immunogenicity profile of individual vaccine epitopes was very similar to the phase 1/2 trials in early-stage NSCLC and colon cancer patient with less burden disease.

Most of the CTL effector/central memory T cells responses in treated patients were induced during the initial 3 to 6-dose/18-week treatment phase and surprisingly as early as after 3 weeks (3 doses). Preferably, the CTL/central memory T cell responses induced during this period, including those directed to Wild Type epitopes, have to be maintained by continued boosting with OSE-2101 sub-cutaneous injections at 2-3 month intervals.

For the remaining 22 patients able to have a leukapheresis and an immunogenicity testing, the overall data indicated that immune monitoring of samples against five of the more immunogenically relevant epitopes in the product (CEA.24V9 (SEQ ID No 3), CEA.605D6 (SEQ ID No9), HER2.369V2V9 (SEQ ID No 4), MAGE3.112I5 (SEQ ID No 8) and MAGE2.157 (SEQ ID No 2)) was sufficient for determining T cell and central memory T cell immunogenicity. The clinical timepoints selected for batch testing were the pre-treatment, Week 9, Week 18 and Week 30 timepoints since most CTL/central memory T cells responses observed among the first 11 patients who were tested indicated were already induced by Week 9 and Week 18 and some were maintained at Week 30.

The immunogenicity of OSE 2101 was similar in phase 2 advanced patients (NSCLC HLA A2 positive patients in advanced stage invasive or metastatic and after at least first line therapy failure) to that observed previously in the two phase 1/2 trials in terms of the overall breadth of CTL+/central memory T cells responses induced in patients and the level of immunogenicity of individual epitopes, thus confirming the overall potency of the product in different patient populations. Multi-epitope CTL+/central memory T cells responses, defined by responses to at least 3 of 5 representative immunogenic epitopes in the OSE-2101 treatment, were observed in 22 of the 33 patients (67%) who were monitored in the phase 2 trial and were achieved as early as Week 9.

TABLE 2

| Antigen | Epitope | week 9 | % | week 18 | % | week 30 | % | month 9 | % | month 12 | % |
|---|---|---|---|---|---|---|---|---|---|---|---|
| CEA | CEA24-ANA | 13/33 | 39% | 10/32 | 31% | 9/23 | 28% | 4/7 | 57% | 2/4 | 50% |
|  | CEA24-WT | 12/33 | 36% | 7/32 | 22% | 5/23 | 22% | 2/7 | 29% | 1/4 | 0% |
|  | CEA605-ANA | 9/33 | 27% | 10/32 | 31% | 8/23 | 35% | 1/7 | 14% | 1/4 | 25% |
|  | CEA605-WT | 10/33 | 30% | 5/32 | 16% | 8/23 | 35% | 1/7 | 14% | 0/4 | 0% |
|  | CEA691-ANA | 7/11 | 64% | 10/11 | 91% | 2/6 | 33% | 3/7 | 43% | 2/4 | 50% |
|  | CEA691-WT | 0/11 | 0% | 0/11 | 0% | 0/6 | 0% | 0/7 | 0% | 0/4 | 0% |
| HER2 | HER2.369-ANA | 14/33 | 42% | 14/32 | 44% | 13/23 | 57% | 2/7 | 29% | 2/4 | 50% |
|  | HER2.369-WT | 11/33 | 33% | 9/32 | 28% | 10/23 | 43% | 2/7 | 29% | 2/4 | 50% |
|  | HER2-689-WT | 4/11 | 36% | 3/11 | 27% | 0/6 | 0% | 0/7 | 0% | 0/4 | 0% |

TABLE 2-continued

| Antigen | Epitope | week 9 | % | week 18 | % | week 30 | % | month 9 | % | month 12 | % |
|---|---|---|---|---|---|---|---|---|---|---|---|
| MAGE | MAGE2.157-WT | 9/33 | 27% | 9/32 | 28% | 10/23 | 43% | 4/7 | 57% | 2/4 | 50% |
|  | MAGE3.112-ANA | 10/33 | 30% | 8/32 | 25% | 10/23 | 43% | 0/7 | 0% | 0/4 | 0% |
|  | MAGE3.112-WT | 10/33 | 30% | 3/32 | 9% | 5/23 | 22% | 0/7 | 0% | 0/4 | 0% |
| p53 | p53.139-ANA | 6/11 | 55% | 4/11 | 36% | 3/6 | 50% | 2/7 | 29% | 2/4 | 50% |
|  | p53.139-WT | 2/11 | 18% | 1/11 | 9% | 0/6 | 0% | 0/7 | 0% | 0/4 | 0% |
|  | p53.149-ANA | 1/11 | 9% | 0/11 | 0% | 0/6 | 0% | 0/7 | 0% | 0/4 | 0% |
|  | p53.149-WT | 0/11 | 0% | 1/11 | 9% | 0/6 | 0% | 0/7 | 0% | 0/4 | 0% |

ANA = Analog peptide, WT = Wild-type peptide

Figure 2:
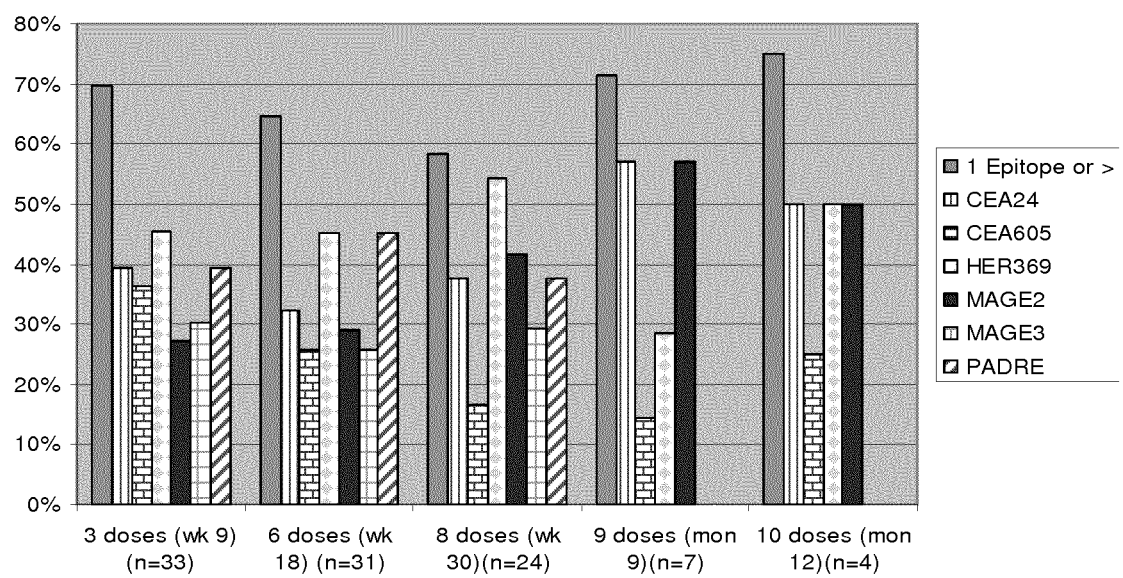
FIG. 2: Phase 2 Central memory T cells responses induced by OSE2101 for several epitopes through the number of doses.

The first 11 patients were tested with all 9 peptide epitopes and the remaining 22 patients were tested with 5 shaded peptide epitopes (CEA24 (SEQ ID No 3), CEA605 (SEQ ID No 9), HER2.369 (SEQ ID No 4), MAGE2.157 (SEQ ID No 2) and MAGE3.112 (SEQ ID No8)). Results are also shown in FIG. 2.

The early W9 response was at the same level as the W18 response and the long term response was still present at one year for patients able to receive a leukapheresis. The long term response was maintained though additive injections.

HTL responses were measured from PBMCs without an in vitro expansion step by standard Elispot. PBMCs were thawed, rested overnight in medium, and $2*10^5$ PBMCs/well were stimulated with 10 µg/mL Pan DR epitope (HTL) or irrelevant malaria peptide in the interferon gamma ELISPOT assay.

IFN-γ producing helper T-cells against PADRE were detected in 18 of 33 patients tested (55%), without short-term in vitro expansion of PBMCs with peptide and was in the same range at Week 9 or Week 18 demonstrating an early HTL response to the epitopes combination.

Figure 3:
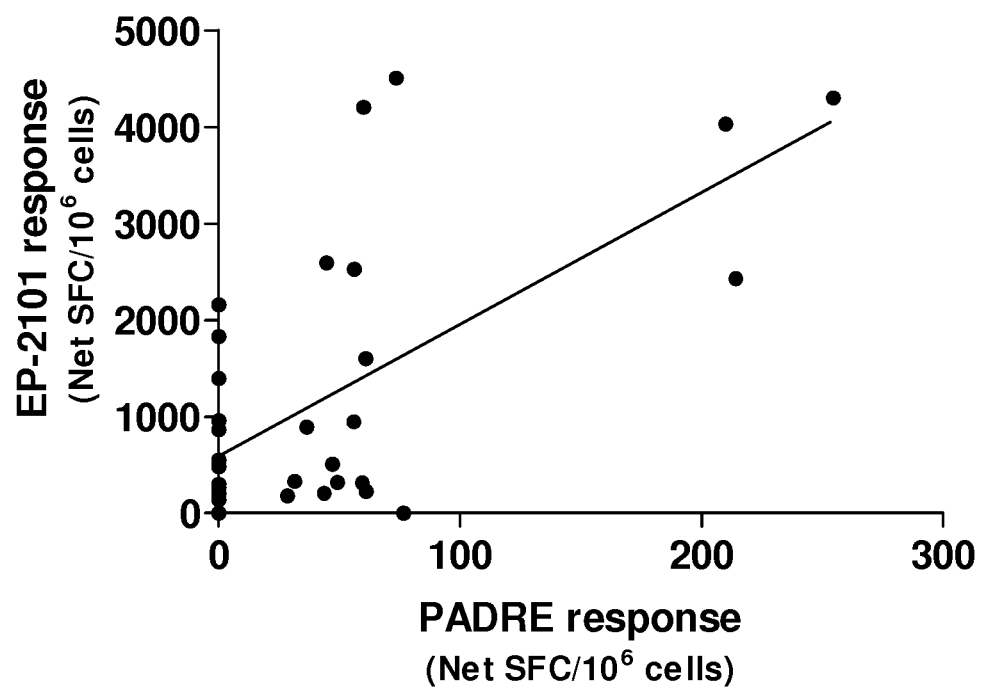
FIG. 3: Correlation between OSE-2101-induced PADRE HTL responses and CTL/central memory T cell responses.
Figure 4:
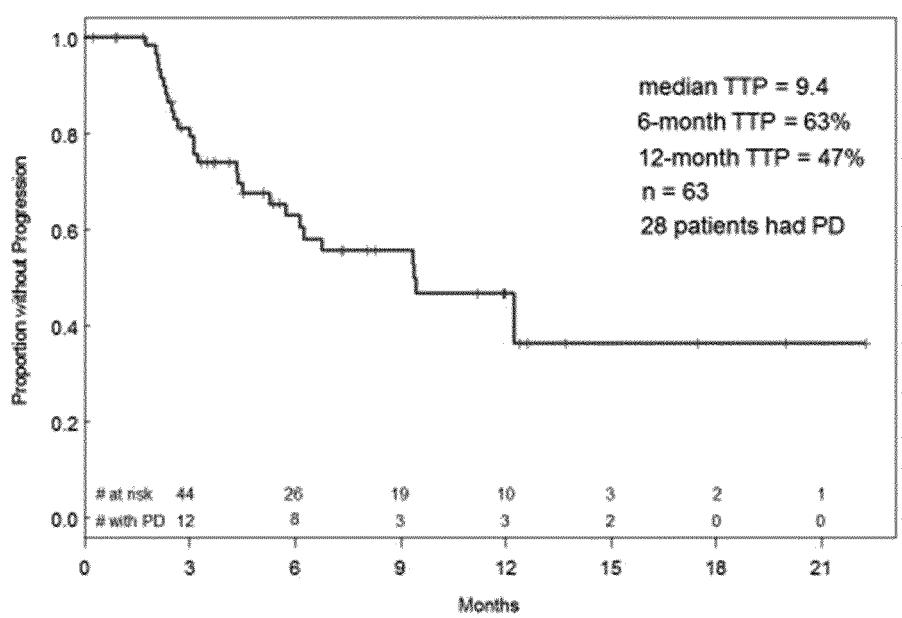
FIG. 4: Kaplan-Meier estimate of TTP.

Then, a correlation between OSE-2101-induced PADRE HTL responses and CTL/central memory T cell responses exists (FIG. 3). The correlation coefficient for this analysis is 0.405.

Example 3

Impact on Time-to-Progression (TTP) Though Early T memory Cells Involvement

TTP results of the short peptide combination in advanced NSCLC after at least first line failure (OSE 2101 phase 2 data internal report). Clinically in oncology, the presence of high levels of infiltrating memory T cells, evaluated immunohistochemically, correlated with the absence of signs of early metastatic invasion, a less advanced pathological stage, and increased survival in 959 specimens of resected colorectal cancer (Pages, F et al, 2005, N Engl J Med; 353:2654-2666). The TTP is interesting as a coherent surrogate item correlated with effector memory T cells for long term and disease free survival.

Sixty-three (63) patients who were HLA-A2 and received OSE-2101 were included in the Time-to-Progression (TTP) analysis. Twenty-eight (28) patients had documented disease progression. Using the Kaplan-Meier estimator, the median time to progression was determined to be 285 days.

The median of the Time to progression (TTP median) after short peptides combination OSE-2101 was 285 days or 9.4 months (SD 86 days). This important clinical item is related to the effector memory CD8+cytotoxic T cells early stimulation (TTP is defined as the time from randomization until objective tumor progression; TTP does not include deaths. PFS is defined as the time from randomization until objective tumor progression or death).

In the same type of advanced NSCLC population (invasive or metastatic) and after at least first line failure (second line treatment), the Progression-Free Survival (PFS) was described at 2.2 months with a Tyrosine kinase inhibitor as Erlotinib (Shepherd F A, et al., 2005, N Engl J Med.; 353, 123-132).

Two chemotherapeutic agents, docetaxel and pemetrexed, and erlotinib are currently approved for the second line treatment of NSCLC patients. The observed TTP in the two clinical phase 3 for docetaxel was between 10.6 and 26 weeks. From pemetrexed phase 3 results, the median PFS was 2.9 months (M A Bareschino; J Thorac Dis 2011; 3:122-133). The median PFS was 3.5 months in the nivolumab phase 3 study in squamous NSCLC (Julie Brahmer, et al, 2015, New England Journal of Medicine May 31).

The unexpected early results of CTL induction through central memory T cell induction by short epitope sequences from tumor antigens of OSE-2101 vaccine, establish the clinical utility of epitopes combination as T specific immunotherapy against cancer and is of particular interest for short term T memory immune responses providing long term efficacy in poor prognosis cancer patients.

Example 4

Results on Advanced Cancer Patients with Malignant Pleural Effusion (MPE)

Patients present an MPE as a complication of far-advanced cancer or as the initial manifestation of an underlying malignancy. Common cancer types causing MPEs include lymphomas, mesotheliomas, and carcinomas of the breast, lung, gastrointestinal tract, and ovaries. The annual incidence of malignant pleural effusions in the United States is estimated to be greater than 150,000 cases. Survival curves for more than 8,000 patients with nonsmall-cell lung cancer (NSCLC) with pleural effusion (i.e., stage IIIB) from the SEER database showed that long-term survival is uncommon in this group. The median survival time is approximately 3 months. Pleural effusion restricts ventilation and causes progressive shortness of breath by compression of lung tissue as well as paradoxical movement of the inverted diaphragm. Pleural deposits of tumor cause pleuritic pain.

Pleural effusions occur more commonly in patients with advanced-stage tumors, who frequently have metastases to the brain, bone, and other organs; physiologic deficits; malnutrition; debilitation; and other comorbidities. Because of these numerous clinical and pathologic variables, it is difficult to perform prospective trials in patients with pleural effusions. For the same reason, it is often difficult to predict a potential treatment outcome or anticipated duration of survival for the specific patient with multiple interrelated clinical problems. Pleural effusion was the first symptom of cancer in 41% of 209 patients with malignant pleural effusion; lung cancer in men (42%) and ovarian cancer in women (27%) were most common.

The discovery of malignant cells in pleural fluid and/or parietal pleura signifies disseminated or advanced disease and a reduced life expectancy in patients with cancer.

In order to understand the role of central memory T cells discovered in phase 2 Cancer patients, the inventors have analyzed retrospectively a sub group of patients presenting Malignant Pleural Effusion. The study was designed to evaluate the safety, efficacy (response and survival), and immunogenicity of OSE-2101 in patients with advanced NSCLC (stage IIIb and IV) who were HLA-A2 positive. The multi-epitope combination was administered subcutaneously at a dose of 5 mg every 3 weeks for the first 15 weeks, then every 2 months through year 1, then quarterly through year 2.

A subgroup of 5 patients was presenting pleural effusion, 2 patients were NSCLC stage IIIB and 3 patients were NSCLC stage IV metastatic.

According to the literature, patients with Malignant Pleural effusions (MPEs) present a severe prognosis with intrathoracic and extrathoracic malignancies. Median survival after diagnosis of an MPE is between 3-4 months. These patients were supposed to have the worse survival time and were thus supposed to be the first to die, shortly in the study.

These 5 patients with MPE were achieving, after receiving the OSE-2101 T specific immunotherapy, a long time without progression and also a very long term survival.

TABLE 4A

MPE on NSCLC Patients description

| | Patient Number | | | | |
|---|---|---|---|---|---|
| | 166 (site 115) NSCLC | 104 (site121) NSCLC | 172 (site 116) NSCLC | 144 (site 217) NSCLC | 170 (site 217) NSCLC |
| gender | female | female | male | male | Female |
| age | 58 Y | 73 Y | 88 Y | 55 Y | 45 Y |
| Ethnic origin | Asian | Caucasian | Caucasian | Caucasian | African American |
| NSCLC Stage | IIIB | IIIB | IV | IV | IV |
| MPE | pleural effusion plus pericardial effusion | Pleural effusion | Pleural effusion | Pleural effusion | Pleural effusion |
| Previous treatments | pericardiocentesis Chest Radiotherapy (10300 cGY) and 1 line of chemotherapy carboplatin + paclitaxel | Thoracentesis Chest RXth (70.2 CGY) and 1 line of chemotherapy Carboplatin + paclitaxel | Chest Radiotherapy (5940 GY) and 1 line of chemotherapy cisplatin + VP16 | Chest RXth (5040 CY) and 4 lines of chemotherapy Carboplatine + paclitaxel Tarceva Topotecan Alimta | Thoracentesis and 3 lines of Carboplatin + paclitaxel + gemzar TRM 1 investigational drug; Tarceva |

TABLE 4B

Time to progression - Survival OS - number of injections

| | Patient Number | | | | |
|---|---|---|---|---|---|
| | 166 NSCLC | 121 NSCLC | 172 NSCLC | 144 NSCLC | 170 NSCLC |
| OS | 20 months | 19 months | 18 months | 6 months | 26 months |
| Time to progression | Stable Disease lost of follow up at 20 months | 19 months | 6 months | 5 months | 3 months |
| CTL + central Memory T cell responses | CTL+/central memory T versus 4 epitopes | CTL+/central memory T Versus 4 epitopes | CTL+/central memory T versus 4 epitopes | Not done | Not done |
| Number of injections | 3 + 9 | 3 + 7 | 3 + 6 | 3 + 2 | 3 |

The time to progression achieved in such poor prognosis MPE population is impressive with a median over than 6 months (3 to 20 months). The median survival achieved is 18 months (6 to 26 months). These long term clinical results are related to an initial priming of 3 injections though the early involvement of central memory T Cells recruiting effector cells CD8+ T cells. In addition, 3 patients/5 are presenting strong positive responses versus 4 epitopes.

The invention claimed is:

1. A method of treating cancer in an HLA-A2 (Human Leukocyte Antigen A2) positive patient, said method comprising a priming period followed by a maintenance period, the priming period consisting of two or three administrations of a therapeutic peptide T specific immune therapy to said patient every two or three weeks during the priming period, thereby inducing a central memory T cell response, and the maintenance period comprising the administration of said therapeutic peptide T specific immune therapy to said patient every two to three months for at least one year, wherein:
   the cancer is a Non Small Cell Lung Cancer (NSCLC) expressing at least one tumor antigen selected from the group consisting of HER2/ErbB2, CEA, p53, MAGE2 and MAGE3, and
   said therapeutic peptide T specific immune therapy comprises the peptides aKXVAAWTLKAAa (SEQ ID No 10), with X and a, respectively, indicating cyclohexylalanine and d-alanine, RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), and YLSGADLNL (SEQ ID No 9).

2. The method according to claim 1, wherein the therapeutic peptide T specific immune therapy consists of the following peptides aKXVAAWTLKAAa (SEQ ID No 10), with X and a respectively indicating cyclohexylalanine and d-alanine, RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5), with B indicating α-aminoisobutyric acid, SMPPPGTRV (SEQ ID No 6), IMIGHLVGV (SEQ ID No 7), KVAEIVHFL (SEQ ID No 8), and YLSGADLNL (SEQ ID No 9).

3. The method according to claim 1, wherein said priming period consists of three administrations of said therapeutic peptide T specific immune therapy.

4. The method according to claim 1, wherein said patient suffers from an advanced or late-stage NSCLC.

5. The method according to claim 1, wherein said patient suffers from metastases.

6. The method according to claim 1, wherein said patient has a malignant pleural effusion.

7. The method according to claim 1, wherein the doses of therapeutic peptide T specific immune therapy are administered parenterally.

8. The method according to claim 1, wherein the peptides are emulsified in incomplete Freund's adjuvant, Montanide ISA-51, mineral oil adjuvant, aluminum hydroxide or alum.

9. The method according to claim 1, wherein the amount of each peptide ranges from 0.1 to 10 mg of peptide in each dose.

10. The method according to claim 9, wherein the amount of total peptide in each dose is 5.0 mg.

11. The method according to claim 1, wherein said patient has already received treatment for the cancer prior to treatment with the therapeutic peptide T specific immune therapy.

12. The method according to claim 1, further comprising administering to the patient an anticancer drug and/or radiotherapy.

13. The method according to claim 1, said method comprising the measurement of central T memory cell response after said priming period and prior to the maintenance period.

14. The method according to claim 13, wherein central T memory response is measured using a IFN-γ enzyme-linked immunospot (cultured ELISPOT) assay.

15. The method according to claim 1, wherein the peptides are administered in combination with GM-CSF as an adjuvant.

* * * * *

```
                         SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Arg Leu Leu Gln Glu Thr Glu Leu Val
1               5

<210> SEQ ID NO 2
<211> LENGTH: 10
<212> TYPE: PRT
<213> ORGANISM: Artificial Sequence
<220> FEATURE:
<223> OTHER INFORMATION: synthetic peptide

<400> SEQUENCE: 2

Tyr Leu Gln Leu Val Phe Gly Ile Glu Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Leu Leu Thr Phe Trp Asn Pro Pro Val
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Lys Val Phe Gly Ser Leu Ala Phe Val
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Xaa is alpha-aminobutyric acid

<400> SEQUENCE: 5

Lys Leu Xaa Pro Val Gln Leu Trp Val
1               5

<210> SEQ ID NO 6
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Ser Met Pro Pro Pro Gly Thr Arg Val
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Ile Met Ile Gly His Leu Val Gly Val
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Lys Val Ala Glu Ile Val His Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

Tyr Leu Ser Gly Ala Asp Leu Asn Leu
1               5

<210> SEQ ID NO 10
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is d-alanine
<220> FEATURE:
<221> NAME/KEY: MISC_FEATURE
<222> LOCATION: (3)..(3)
<223> OTHER INFORMATION: Xaa is a cyclohexylalanine
<220> FEATURE:
<221> NAME/KEY: MISC_FEATURE
<222> LOCATION: (13)..(13)
<223> OTHER INFORMATION: Xaa is d-alanine

<400> SEQUENCE: 10

Xaa Lys Xaa Val Ala Ala Trp Thr Leu Lys Ala Ala Xaa
1               5                   10

<210> SEQ ID NO 11
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 11

Ala Leu Leu Glu Ile Ala Ser Cys Leu
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic peptide

<400> SEQUENCE: 12

Gly Leu Cys Thr Leu Val Ala Met Leu
1               5
```